United States Patent [19]

Takago et al.

[11] Patent Number: 4,652,663

[45] Date of Patent: Mar. 24, 1987

[54] NOVEL ORGANOSILICON COMPOUND

[75] Inventors: Toshio Takago; Yasushi Yamamoto; Koichi Yamaguchi; Hideto Kato, all of Gunma, Japan

[73] Assignee: Shin-Etsu Chemical Co., Ltd., Japan

[21] Appl. No.: 862,676

[22] Filed: May 13, 1986

[30] Foreign Application Priority Data

May 16, 1985 [JP] Japan .................................. 60-104627

[51] Int. Cl.$^4$ ............................ C07F 7/08; C07F 7/10; C07F 7/18; C07D 303/02
[52] U.S. Cl. ..................................... 549/215; 556/415; 556/429; 556/440; 556/485
[58] Field of Search ................ 556/485, 415, 429, 440; 549/215

[56] References Cited

U.S. PATENT DOCUMENTS

| | | | |
|---|---|---|---|
| 2,892,859 | 6/1959 | McBee et al. | 556/485 |
| 2,928,857 | 3/1960 | Holt et al. | 556/485 |
| 3,394,162 | 7/1968 | Braun | 549/215 X |
| 3,536,744 | 10/1970 | Dear | 556/485 |
| 3,687,606 | 8/1972 | Simmler et al. | 549/215 X |
| 4,069,368 | 1/1978 | Deyak et al. | 549/215 X |

Primary Examiner—Paul F. Shaver
Attorney, Agent, or Firm—Toren, McGeady and Goldberg

[57] ABSTRACT

A class of novel organosilane compounds are disclosed as represented by the general formula

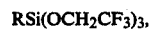

$$RSi(OCH_2CF_3)_3,$$

in which R is an atom or group selected from the class consisting of a hydrogen atom, unsaturated monovalent aliphatic hydrocarbon groups having from 2 to 20 carbon atoms, monovalent aryl groups and monovalent organic groups having from 3 to 20 carbon atoms and containing at least one hetero atom, i.e. an atom other than carbon and hydrogen atoms, such as oxygen, halogens, sulfur and nitrogen, the said hetero atom-containing organic group being bonded to the silicon atom through a carbon-to-silicon linkage. Several particular compounds belonging to the class were synthesized and identified.

11 Claims, No Drawings

NOVEL ORGANOSILICON COMPOUND

BACKGROUND OF THE INVENTION

The present invention relates to a novel organosilicon compound or, more particularly, to a class of novel organosilicon compounds containing fluorine atoms neither known in the prior art nor described in any literatures. The organosilicon compounds of the invention have high compatibility or miscibility with various kinds of fluorine-containing rubbers and plastic resins to serve as a crosslinking agent or adhesion aid.

Various kinds of fluorine-containing organosilicon compounds are known in the organosilicon chemistry including, for example, fluorine-containing alkoxysilanes such as 2,2,2-tri-fluoroethoxy-containing silanes disclosed in U.S. Pat. No. 2,892,859 and useful as an additive in fire-extinguishing agents, lubricants and the like. The organic groups other than the 2,2,2-trifluoroethoxy group bonded to the silicon atom of the silane compound, however, are limited to aliphatic saturated hydrogen groups or alkyl groups such as methyl, ethyl and isopropyl groups.

SUMMARY OF THE INVENTION

The novel organosilicon compounds or organosilane compounds of the invention are represented, as a class, by the general formula $$RSi(OCH_2CF_3)_3, \quad (1)$$

in which R is an atom or group selected from the class consisting of a hydrogen atom, unsaturated monovalent aliphatic hydrocarbon groups having from 2 to 20 carbon atoms, monovalent aryl groups and monovalent organic groups having from 3 to 20 carbon atoms and containing at least one hetero atom, i.e. an atom other than carbon and hydrogen atoms, such as oxygen, halogens, sulfur and nitrogen, the said hetero atom-containing organic group being bonded to the silicon atom through a carbon-to-silicon linkage.

Particular examples of the organosilane compounds in conformity with the above given definition include:

(A) tris(2,2,2-trifluoroethoxy) silane of the formula HSi(OCH$_2$CF$_3$)$_3$;

(B) vinyl tris(2,2,2-trifluoroethoxy) silane of the formula CH$_2$=CHSi(OCH$_2$CF$_3$)$_3$;

(C) phenyl tris(2,2,2-trifluoroethoxy) silane of the formula C$_6$H$_5$Si(OCH$_2$CF$_3$)$_3$;

(D) 3-glycidyloxypropyl tris(2,2,2-trifluoroethoxy) silane of the formula

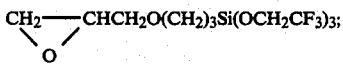
CH$_2$——CHCH$_2$O(CH$_2$)$_3$Si(OCH$_2$CF$_3$)$_3$;

(E) 3-methacryloxypropyl tris(2,2,2-trifluoroethoxy) silane of the formula CH$_2$=C(CH$_3$)—CO—O(CH$_2$)$_3$Si(OCH$_2$CF$_3$)$_3$;

(F) 3-chloropropyl tris(2,2,2-trifluoroethoxy) silane of the formula Cl(CH$_2$)$_3$Si(OCH$_2$CF$_3$)$_3$;

(G) 3-mercaptopropyl tris(2,2,2-trifluoroethoxy) silane of the formula HS(CH$_2$)$_3$Si(OCH$_2$CF$_3$)$_3$;

(H) 3,3,3-trifluoropropyl tris(2,2,2-trifluoroethoxy) silane of the formula CF$_3$CH$_2$CH$_2$Si(OCH$_2$CF$_3$)$_3$; and (I) 2-cyanoethyl tris(2,2,2-trifluoroethoxy) silane of the formula NC—CH$_2$CH$_2$Si(OCH$_2$CF$_3$)$_3$.

DETAILED DESCRIPTION OF THE PREFERRED EMBODIMENTS

As is summarized above, the novel organosilane compounds of the invention as a class can be represented by the above given general formula (1), in which the symbol R has the meaning as defined above. Namely, the symbol R in the formula denotes an atom or group selected from the class consisting of:

(i) a hydrogen atom directly bonded to the silicon atom;

(ii) an unsaturated monovalent aliphatic hydrocarbon group having from 2 to 20 carbon atoms, e.g. vinyl and allyl groups;

(iii) a monovalent aryl group, e.g. phenyl and tolyl groups; and (iv) a monovalent organic group having from 3 to 20 carbon atoms and containing at least one hetero atom, i.e. an atom other than carbon and hydrogen atoms, such as oxygen, halogens, sulfur and nitrogen, the said hetero atom-containing organic group being bonded to the silicon atom through a carbon-to-silicon linkage, exemplified by 3-glycidyloxypropyl, 3-methacryloxypropyl, 3-chloropropyl, 3-mercaptopropyl, 3,3,3-trifluoropropyl and 2-cyanoethyl groups. Accordingly, the inventive organosilane compounds include the above named particular compounds (A) to (I) as the typical examples.

The organosilane compound of the invention can be synthesized, for example, by the dehydrochlorination reaction between a trichlorosilane compound of the formula RSiCl$_3$, R having the same meaning as defined above, and 2,2,2-trifluoroethyl alcohol of the formula CF$_3$CH$_2$OH according to the following reaction equation:

$$RSiCl_3 + 3\ CF_3CH_2OH \rightarrow RSi(OCH_2CF_3)_3 + 3\ HCl.$$

The 2,2,2-trifluoroethyl alcohol should be used in an amount of at least 3.0 moles or, preferably, in the range from 3.2 to 4.0 moles per mole of the trichlorosilane compound. The reaction temperature should be adequately selected depending on the kind of the group denoted by R. For example, the temperature should be in the range from −15° to −10° C. when R is a silicon-bonded hydrogen atom and in the range from 10° C. to room temperature when R is a substituted or unsubstituted hydrocarbon group.

The novel organosilicon compounds of the invention have high compatibility or miscibility with fluorocarbon polymers such as fluorocarbon rubbers and resins so that the compounds are useful as an additive in the fluorocarbon polymers as well as a coupling agent to aid adhesive bonding of the fluorocarbon polymer to other materials. In particular, the inventive organosilane compounds are useful as an odorless crosslinking agent to replace acetoxy silanes used in room temperature-curable fluorosilicone rubbers.

In the following, examples are given to illustrate the preparation and characterization of the inventive organosilane compounds in more detail.

EXAMPLE 1

Into 200 g (1.47 moles) of trichlorosilane HSiCl$_3$ taken in a flask and kept at a temperature of −15° C. were added dropwise 590 g (5.9 moles) of 2,2,2-trifluoroethyl alcohol over a period of 2 hours while the hydrogen chloride gas produced by the reaction was continuously removed from the reaction mixture by suction with an aspirator. After completion of the dropwise addition of the reagent, the hydrogen chloride dissolved in the reaction mixture was removed as completely as possible under reduced pressure and the mixture in the flask was subjected to distillation under normal pressure to give 340 g of a liquid product boiling at 136° C.

This product was analyzed by elementary analysis, gas chromatographic-mass spectrometric (GC-MS) analysis, infrared absorption spectrophotometry and NMR absorption spectrometry to give the results shown below, from which the compound could be identified to be tris(2,2,2-trifluoroethoxy) silane. The above mentioned yield corresponds to 70.7% of the theoretical value based on the amount of the starting trichlorosilane.

| Elementary analysis | C | H | Si | F |
|---|---|---|---|---|
| Calculated as $C_6H_7O_3F_9Si$, % | 22.09 | 2.16 | 8.61 | 52.42 |
| Found, % | 22.07 | 2.14 | 8.63 | 52.44 |

GC-MS analysis (molecular weight)
326 (calculated value 326 for $C_6H_7O_3F_9Si$)
Infrared absorption spectrum
2,250 cm$^{-1}$ (assigned to —Si—H)
NMR absorption spectrum ($\delta$ value, ppm, in $CCl_4$, with $CHCl_3$ as the internal standard)
4.53 (s, 1H, Si—H)
4.05–4.20 (q, 6H, $SiOCH_2CF_3$)

EXAMPLE 2

Into 200 g (2.0 moles) of 2,2,2-trifluoroethyl alcohol in a flask were added dropwise 80.8 g (0.5 mole) of vinyl trichlorosilane while the hydrogen chloride gas produced by the reaction was continousuly removed out of the reaction mixture by passing a gentle stream of nitrogen gas as a carrier through the flask. After completion of the dropwise addition of the silane compound, the reaction mixture was further agitated for 6 hours at 15° C. to complete the reaction. After purging the hydrogen chloride out of the flask, dry urea was added to the reaction mixture to neutralize the residual trace amount of hydrogen chloride followed by filtration of the mixture to remove the urea and the hydrogenchloride thereof and the filtrate was subjected to distillation under normal pressure to give 129 g of a liquid product boiling at 151° C.

This product was analyzed by elementary analysis, gas chromatographic-mass spectrometric (GC-MS) analysis, infrared absorption spectrophotometry and NMR absorption spectrometry to give the results shown below, from which the compound could be identified to be vinyl tris(2,2,2-trifluoroethoxy) silane. The above mentioned yield corresponds to 73.3% of the theoretical value based on the amount of the starting vinyl trichlorosilane.

| Elementary analysis | C | H | Si | F |
|---|---|---|---|---|
| Calculated as $C_8H_9O_3F_9Si$, % | 27.28 | 2.56 | 7.97 | 48.54 |
| Found, % | 27.31 | 2.55 | 7.95 | 48.51 |

GC-MS analysis (molecular weight)
352 (calculated value 352 for $C_8H_9O_3F_9Si$)
Infrared absorption spectrum
1,600 cm$^{-1}$ (assigned to —CH=CH$_2$)
1,800 cm$^{-1}$ (assigned to —CH=CH$_2$)
1,300 cm$^{-1}$ (assigned to —CH$_2$—CF$_3$)
NMR absorption spectrum ($\delta$ value, ppm, in $CCl_4$, with $CHCl_3$ as the internal standard)
5.68–6.44 (m, 3H, CH$_2$=CHSi)
4.02–4.28 (q, 6H, $SiOCH_2CF_3$)

EXAMPLE 3

The procedure of synthetic preparation was substantially the same as in Example 2 using 52.9 g (0.25 mole) of phenyl trichlorosilane and 100 g (1.0 mole) of 2,2,2-trifluoroethyl alcohol as the reactants to give 92.6 g of a liquid product boiling at 100° C. under normal pressure.

This product was analyzed by elementary analysis, gas chromatographic-mass spectrometric (GC-MS) analysis, infrared absorption spectrophotometry and NMR absorption spectrometry to give the results shown below, from which the compound could be identified to be phenyl tris(2,2,2-trifluoroethoxy) silane. The above mentioned yield corresponds to 72.4% of the theoretical value based on the amount of the starting phenyl trichlorosilane.

| Elementary analysis | C | H | Si | F |
|---|---|---|---|---|
| Calculated as $C_{12}H_{11}O_3F_9Si$, % | 35.83 | 2.76 | 6.98 | 42.50 |
| Found, % | 35.80 | 2.81 | 6.94 | 42.48 |

GC-MS analysis (molecular weight)
402 (calculated value 402 for $C_{12}H_{11}O_3F_9Si$)
Infrared absorption spectrum
1,595 cm$^{-1}$ (assigned to $C_6H_5$—Si)
1,435 cm$^{-1}$ (assigned to $C_6H_5$—Si)
NMR absorption spectrum ($\delta$ value, ppm, in $CCl_4$, with $CHCl_3$ as the internal standard)
7.56–7.92 (m, 5H, $C_6H_5$—Si—)
4.24–4.48 (q, 6H, $SiOCH_2CF_3$)

EXAMPLE 4

A mixture composed of 22.7 g (0.2 mole) of allyl glycidyl ether, 50 g of toluene and 0.015 g of an isopropyl alcohol solution of chloroplatinic acid containing 2.0% by weight of platinum in a flask was heated and kept at 80° C. and 50 g (0.015 mole) of tris(2,2,2-trifluoroethoxy) silane were added thereto dropwise over a period of about 2 hours. After completion of the dropwise addition of the silane compound, the reaction mixture was further heated at 80° to 90° C. under agitation for 8 hours to complete the reaction and the reaction mixture was then subjected to distillation under reduced pressure to give 60 g of a liquid product boiling at 115° C. under Ra pressure of 3 mmHg.

This product was analyzed by elementary analysis, gas chromatographic-mass spectrometric (GC-MS) analysis and NMR absorption spectrometry to give the results shown below, from which the compound could be identified to be 3-glycidyloxypropyl tris(2,2,2-trifluoroethoxy) silane. The above mentioned yield corresponds to 88.9% of the theoretical value based on the amount of the starting tris(2,2,2-trifluoroethoxy) silane.

| Elementary analysis | C | H | Si | F |
|---|---|---|---|---|
| Calculated as $C_{12}H_{17}O_5F_9Si$, % | 32.73 | 3.89 | 6.38 | 38.83 |
| Found, % | 32.68 | 3.94 | 6.45 | 38.77 |

-continued

| Elementary analysis | C | H | Si | F |
|---|---|---|---|---|

GC-MS analysis (molecular weight)
440 (calculated value 440 for $C_{12}H_{17}O_5F_9Si$)
NMR absorption spectrum (δ value, ppm, in $CCl_4$, with $CHCl_3$ as the internal standard)

2.44–2.52 (dd, 1H, O—CH$_2$—— H +)
   $|\diagdown O \diagup |$
   H       H 2.64–2.72 (dd, 1H, OCH$_2$——H)
   $|\diagdown O \diagup |$
   H       H 2.94–3.10 ( , 1H, CH$_2$——CH—)
   $\diagdown O \diagup$ 3.44–3.50 ( , 2H, CH$_2$——CH—CH$_2$—O)
   $\diagdown O \diagup$ 3.32–3.44 (t, 2H, —OC$\underline{H}_2$CH$_2$CH$_2$Si)

1.56–1.84 (m, 2H, —OCH$_2$C$\underline{H}_2$CH$_2$Si)

0.80–0.96 (t, 2H, —OCH$_2$CH$_2$C$\underline{H}_2$Si)

3.98–4.22 (q, 6H, SiOCH$_2$CF$_3$)

EXAMPLE 5

Reaction of 91 g (0.35 mole) of 3-methacryloxypropyl trichlorosilane and 140 g (1.4 moles) of 2,2,2-trifluoroethyl alcohol was undertaken in the same manner as in Example 2 followed by processing of the reaction mixture to give 118 g of a liquid product boiling at 134° C. under a pressure of 5 mmHg.

This product was analyzed by elementary analysis, gas chromatographic-mass spectrometric (GC-MS) analysis, infrared absorption spectrophotometry and NMR absorption spectrometry to give the results shown below, from which the compound could be indentified to be 3-methacryloxypropyl tris(2,2,2-trifluoroethoxy) silane. The above mentioned yield corresponds to 74.8% of the theoretical value based on the amount of the starting 3-methacryloxypropyl trichlorosilane.

| Elementary analysis | C | H | Si | F |
|---|---|---|---|---|
| Calculated as $C_{13}H_{17}O_5F_9Si$, % | 34.52 | 3.79 | 6.21 | 37.80 |
| Found, % | 34.50 | 3.84 | 6.25 | 37.77 |

GC-MS analysis (molecular weight)
452 (calculated value 452 for $C_{13}H_{17}O_5F_9Si$)
Infrared absorption spectrum
1,720 cm$^{-1}$ (assigned to —CO—O—)

1,640 cm$^{-1}$ (assigned to CH$_2$=C$\diagup^{CH_3}_{\diagdown}$ )

NMR absorption spectrum (δ value, ppm, in $CCl_4$, with $CHCl_3$ as the internal standard)
5.50   (s, 1H, CH$_2$=C)
6.04   (s, 1H, CH$_2$=C)
1.38   (s, 3H, C=CCH$_3$)

4.04–4.20 (t, 2H, CO—OC$\underline{H}_2$CH$_2$CH$_2$Si)

1.62–1.90 (m, 2H, CO—OCH$_2$C$\underline{H}_2$CH$_2$Si)

-continued

| Elementary analysis | C | H | Si | F |
|---|---|---|---|---|

0.73–0.90 (m, 2H, CO—OCH$_2$CH$_2$C$\underline{H}_2$Si)

4.00–4.24 (q, 6H, SiOCH$_2$CF$_3$)

EXAMPLE 6

Reaction of 162 g (0.75 mole) of 3-chloropropyl trichlorosilane and 300 g (3.0 moles) of 2,2,2-trifluoroethyl alcohol was undertaken in the same manner as in Example 2 followed by processing of the reaction mixture to give 217 g of a liquid product boiling at 123° C. under a pressure of 30 mmHg.

This product was analyzed by elementary analysis, gas chromatographic-mass spectrometric (GC-MS) analysis and NMR absorption spectrometry to give the results shown below, from which the compound could be identified to be 3-chloropropyl tris(2,2,2-trifluoroethoxy) silane. The above mentioned yield corresponds to 71.3% of the theoretical value based on the amount of the starting 3-chloropropyl trichlorosilane.

| Elementary analysis | C | H | Si | F |
|---|---|---|---|---|
| Calculated as $C_9H_{12}O_3ClF_9Si$, % | 26.84 | 3.00 | 6.97 | 42.46 |
| Found, % | 26.81 | 2.95 | 7.05 | 42.41 |

GC-MS analysis (molecular weight)
403 (calculated value 403 for $C_9H_{12}O_3ClF_9Si$)
NMR absorption spectrum (δ value, ppm, in $CCl_4$, with $CHCl_3$ as the internal standard)
3.48–3.61 (t, 2H, ClC$\underline{H}_2$CH$_2$CH$_2$Si)
1.80″2.12 (m, 2H, ClCH$_2$C$\underline{H}_2$CH$_2$Si)
0.90–1.07 (m, 2H, ClCH$_2$CH$_2$C$\underline{H}_2$Si)
4.02–4.28 (q, 6H, SiOCH$_2$CF$_3$)

EXAMPLE 7

Into a flask were introduced 90 g (0.22 mole) of 3-chloropropyl tris(2,2,2-trifluoroethoxy) silane and 19.9 g (0.26 mole) of thiourea and the mixture was heated under agitation at 80° to 90° C. for 24 hours to form a thiuronium salt, into which ammonia gas was blown for 15 hours to be reacted. The reaction mixture was filtered and the filtrate was distilled under reduced pressure to give 15 g of a liquid product boiling at 86° C. under a pressure of 5 mmHg.

This product was analyzed by elementary analysis, gas chromatographic-mass spectrometric (GC-MS) analysis, infrared absorption spectrophotometry and NMR absorption spectrometry to give the results shown below, from which the compound could be identified to be 3-mercaptopropyl tris(2,2,2-trifluoroethoxy) silane.

| Elementary analysis | C | H | Si | F |
|---|---|---|---|---|
| Calculated as $C_9H_{13}O_3F_9SSi$, % | 27.00 | 3.27 | 7.02 | 42.71 |
| Found, % | 26.99 | 3.25 | 7.05 | 42.68 |

GC-MS analysis (molecular weight)
400 (calculated value 400 for $C_9H_{13}O_3F_9SSi$)
Infrared absorption spectrum
2,580 cm$^{-1}$ (assigned to —SH)
NMR absorption spectrum (δ value, ppm, in $CCl_4$, with $CHCl_3$ as the internal standard)
1.17–1.35 (t, 1H, HS—)
2.47–2.72 (dt, 1H, —SC$\underline{H}_2$CH$_2$CH$_2$Si)

| Elementary analysis | C | H | Si | F |
|---|---|---|---|---|
| 1.62–1.92 (m, 2H, —SCH$_2$C$\underline{H}_2$CH$_2$Si) | | | | |
| 0.88–1.04 (m, 2H, —SCH$_2$CH$_2$C$\underline{H}_2$Si) | | | | |
| 4.02–4.26 (q, 6H, SiOCH$_2$CF$_3$) | | | | |

EXAMPLE 8

Reaction of 151 g (0.65 mole) of 3,3,3-trifluoropropyl trichlorosilane and 260 g (2.6 moles) of 2,2,2-trifluoroethyl alcohol was undertaken in the same manner as in Example 2 followed by processing of the reaction mixture to give 198 g of a liquid product boiling at 107° C. under a pressure of 50 mmHg.

This product was analyzed by elementary analysis, gas chromatographic-mass spectrometric (GC-MS) analysis and NMR absorption spectrometry to give the results shown below, from which the compound could be identified to be 3,3,3-trifluoropropyl tris(2 2 2-trifluoroethoxy) silane. The above mentioned yield corresponds to 70.5% of the theoretcial value based on the amount of the starting 3,3,3-trifluoropropyl trichlorosilane.

| Elementary analysis | C | H | Si | F |
|---|---|---|---|---|
| Calculated as | | | | |
| C$_9$H$_{10}$O$_3$F$_{12}$Si, % | 25.60 | 2.39 | 6.65 | 53.99 |
| Found, % | 25.55 | 2.44 | 6.66 | 53.95 |
| GC-MS analysis (molecular weight) | | | | |
| 422 (calculated value 422 for C$_9$H$_{10}$O$_3$F$_{12}$Si) | | | | |
| NMR absorption spectrum ($\delta$ value, ppm, in CCl$_4$, with CHCl$_3$ as the internal standard) | | | | |
| 1.96–2.44 (m, 2H, CF$_3$C$\underline{H}_2$CH$_2$Si) | | | | |
| 0.96–1.15 (m, 2H, CF$_3$CH$_2$C$\underline{H}_2$Si) | | | | |
| 4.04–4.28 (q, 6H, SiOCH$_2$CF$_3$) | | | | |

EXAMPLE 9

Reaction of 142 g (0.75 mole) of 2-cyanoethyl trichlorosilane and 300 g (3.0 moles) of 2,2,2-trifluoroethyl alcohol was undertaken in the same manner as in Example 2 followed by processing of the reaction mixture to give 202 g of a liquid product boiling at 98° C. under a pressure of 3 mmHg.

This product was analyzed by elementary analysis, gas chromatographic-mass spectrometric (GC-MS) analysis, infrared absorption spectrophotometry and NMR absorption spectrometry to give the results shown below, from which the compound could be identified to be 2-cyanoethyl tris(2,2,2-trifluoroethoxy) silane. The above mentioned yield corresponds to 71.4% of the theoretical value based on the amount of the starting 2-cyanoethyl trichlorosilane.

| Elementary analysis | C | H | Si | F |
|---|---|---|---|---|
| Calculated as | | | | |
| C$_9$H$_{10}$O$_3$NF$_9$Si, % | 28.58 | 2.66 | 7.41 | 45.08 |
| Found, % | 28.51 | 2.66 | 7.43 | 45.03 |
| GC-MS analysis (molecular weight) | | | | |
| 379 (calculated value 379 for C$_9$H$_{10}$O$_3$NF$_9$Si) | | | | |
| Infrared absorption spectrum | | | | |
| 2,250 cm$^{-1}$ (assigned to —C≡N)  | | | | |
| NMR absorption spectrum ($\delta$ value, ppm, in CCl$_4$, with CHCl$_3$ as the internal standard) | | | | |
| 2.35–2.50 (t, 2H, NCC$\underline{H}_2$CH$_2$Si) | | | | |
| 1.10–1.26 (m, 2H, NCCH$_2$C$\underline{H}_2$Si) | | | | |
| 4.40–4.28 (q, 6H, SiOCH$_2$CF$_3$) | | | | |

What is claimed is:

1. An organosilane compound represented by the general formula

RSi(OCH$_2$CF$_3$)$_3$, in which R is an atom or group selected from the class consisting of a hydrogen atom, unsaturated monovalent aliphatic hydrocarbon groups having from 2 to 20 carbon atoms, monovalent aryl groups and monovalent organic groups having from 3 to 20 carbon atoms and containing at least one hetero atom, the said hetero atom-containing organic group being bonded to the silicon atom through a carbon-to-silicon linkage.

2. The organosilane compound as claimed in claim 1 wherein the hetero atom is selected from the class consisting of atoms of oxygen, halogens, sulfur and nitrogen.

3. Tris(2,2,2-trifluoroethoxy) silane of the formula HSi(OCH$_2$CF$_3$)$_3$.

4. Vinyl tris(2,2,2-trifluoroethoxy) silane of the formula CH$_2$=CHSi(OCH$_2$CF$_3$)$_3$.

5. Phenyl tris(2,2,2-trifluoroethoxy) silane of the formula C$_6$H$_5$S(OCH$_2$CF$_3$)$_3$.

6. 3-Glycidyloxypropyl tris(2,2,2-trifluoroethoxy) silane of

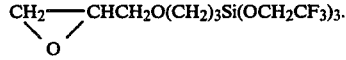

7. 3-Methacryloxypropyl tris(2,2,2-trifluoroethoxy) silane of the formula CH$_2$=C(CH$_3$)—CO—O(CH$_2$)$_3$Si(OCH$_2$CF$_3$)$_3$.

8. 3-Chloropropyl tris(2,2,2-trifluoroethoxy) silane of the formula Cl(CH$_2$)$_3$Si(OCH$_2$CF$_3$)$_3$.

9. 3-Mercaptopropyl tris(2,2,2-trifluoroethoxy) silane of the formula HS(CH$_2$)$_3$Si(OCH$_2$CF$_3$)$_3$.

10. 3,3,3-Trifluoropropyl tris(2,2,2-trifluoroethoxy) silane of the formula CF$_3$CH$_2$CH$_2$Si(OCH$_2$CF$_3$)$_3$.

11. 2-Cyanoethyl tris(2,2,2-trifluoroethoxy) silane of the formula NC—CH$_2$CH$_2$Si(OCH$_2$CF$_3$)$_3$.

* * * * *